Figure 3:
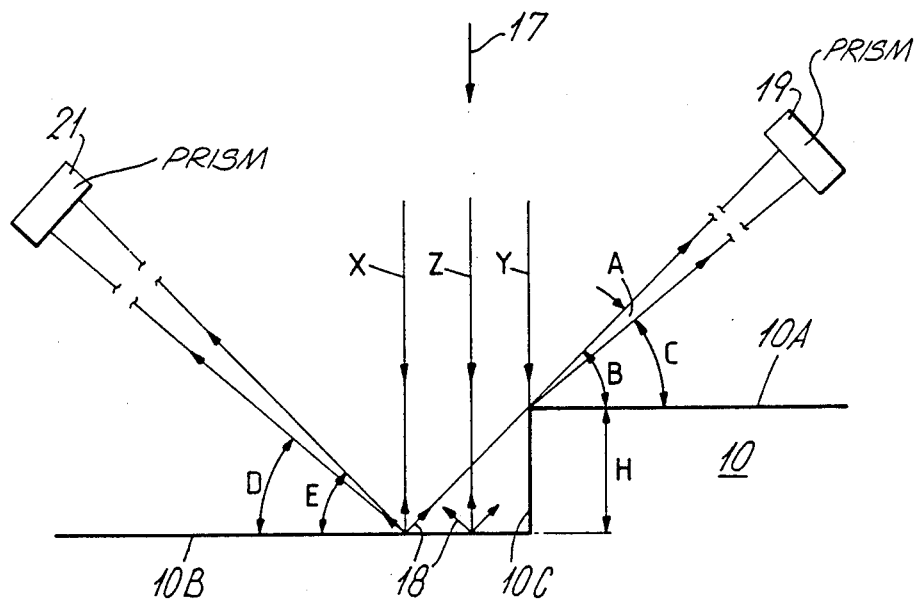

United States Patent [19]

West

[11] Patent Number: 4,851,696
[45] Date of Patent: Jul. 25, 1989

[54] APPARATUS FOR RECEIVING RADIATION ONLY WITHIN PREDETERMINED ANGULAR LIMITS

[75] Inventor: Robert N. West, Chislehurst, Great Britain

[73] Assignee: Sira Limited, Kent, Great Britain

[21] Appl. No.: 42,227

[22] Filed: Apr. 15, 1987

[30] Foreign Application Priority Data

Apr. 28, 1986 [GB] United Kingdom ................ 8610304

[51] Int. Cl.⁴ ...................... G01N 21/88; G01N 21/89
[52] U.S. Cl. ................................... 250/572; 356/237; 356/430; 250/216
[58] Field of Search ............... 250/562, 563, 572, 216; 356/237, 430, 431

[56] References Cited

U.S. PATENT DOCUMENTS 4,004,152  1/1977  Obser et al. ........................ 250/572
4,378,159  3/1983  Galbraith ............................ 356/237
4,601,576  7/1986  Galbraith ............................ 250/572

FOREIGN PATENT DOCUMENTS 472448   9/1937  United Kingdom.
1044950  10/1966  United Kingdom.
2117897  10/1983  United Kingdom.

Primary Examiner—Edward P. Westin
Attorney, Agent, or Firm—Christie, Parker & Hale

[57] ABSTRACT

Apparatus for detecting discontinuities in a radiation diffusing surface (10) such as paper. Radiation is passed to the surface and a radiation collector (19) receives the diffused radiation (18) from a limited area of the surface (10). The radiation collector receives the diffuse radiation from a limited area only and from within predetermined angular limits other than normal to the surface. The radiation collector (19) defines said predetermined angular limits through total internal reflection.

11 Claims, 2 Drawing Sheets

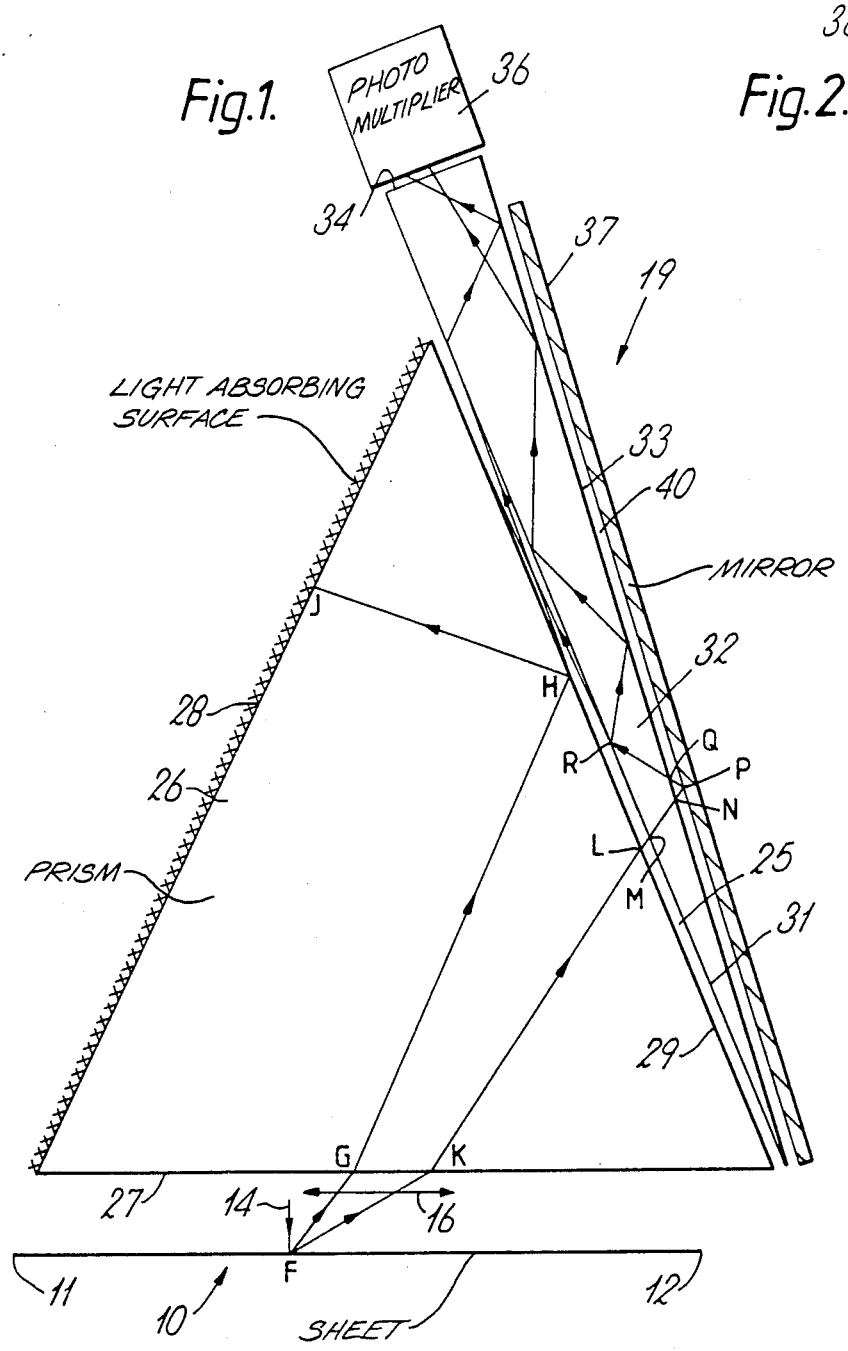

APPARATUS FOR RECEIVING RADIATION ONLY WITHIN PREDETERMINED ANGULAR LIMITS

The present invention relates to an optical apparatus and method for examining an object. Many methods for examining objects optically have been proposed and they frequently comprise means for scanning radiation across the object under examination and collecting the radiation influenced by the object to determine features including faults or flaws in the object.

A particular problem which arises in examining some objects having a generally flat surface (such as sheet material) is to detect, by optical inspection apparatus, discontinuities in the surface such as creases or abrupt changes in surface level.

Two examples may be given but there are many others. In the manufacture of sheet material creases can occur in the material which provide an abrupt change of the surface of the material. Secondly, in the production of newspapers, before printing, a mock-up of the newspaper is produced which comprises a sheet of paper the size of the finished product and glued to this paper are a number of other pieces of paper carrying some of the various articles which are to appear on the page. The reason they are produced separately is during the planning of that page of the newspaper. A problem arises in printing the newspaper from this mock-up in that where the separate pieces of paper appear stuck on to the large sheet of paper there are provided discontinuities in the form of edges. This problem is particularly acute in a case where the image of the page is to be transmitted to a remote location in the form of a linear digital (or analogue) signal which is produced by scanning across the page and detecting, during the scan, the light signal reflected or otherwise influenced by the surface of the paper. Clearly one wishes to pass signals which correspond to the blank paper and to the print since that will reproduce the image but it is possible with this system that the shadows caused by edges between the sheets of paper which have been stuck on to the large sheet of paper will also be reproduced and this is clearly undesirable.

Such edges which are caused by abrupt changes of surface level also occur in other situations where an object is to be examined and in some circumstances it is desirable to be able to obtain some indication of the extent of change of the surface level. For example, a certain degree of tolerance of change of surface level may be permissable when dealing with, for example, pits or craters in a surface.

An earlier arrangement is described in our British Patent Specification No. 2117897. In this, radiation is reflected from a radiation diffusing surface is collected from a predetermined dirrection other than normal to the surface by a variety of means which one can summarize as being of a "Venetian blind" type.

The present invention provides according to one aspect an optical apparatus for receiving radiation within defined angular limits, the optical apparatus including optical means through which the radiation is passed and in which the radiation is internally reflected, and the opposite angular limits of the receipt of radiation are defined by total internal reflection.

The apparatus also provides an optical apparatus as claimed in claim 1 of our U.S. Pat. No. 2,117,897 in which the radiation collection means includes means for defining said one or more predetermined directions by means of total internal reflection.

Throughout the specification we shall refer to "light" and "optical". The normal arrangement uses visible light, but it is possible to operate the invention with radiation of other wavelengths such as infra red or ultra violet and the words light and optical should be interpreted accordingly.

Preferred embodiments of the invention will now be described by way of example only and with reference to the accompanying drawings in which:

FIG. 1 is a front view of a light collection apparatus according to a first aspect of the invention, FIG. 2 is a side view of the apparatus of FIG. 1, FIG. 3 is a enlarged section of part of a surface to be examined showing the method of operation of the invention.

Referring to FIG. 1 the object to be examined comprises a diffuse surface which may be, by way of example only, a sheet of material 10 the width of which is illustrated in FIG. 1 between points 11 and 12 and which moves in a direction shown by the arrow 13 in FIG. 2. The sheet of material may comprise paper, textile or the like. The sheet 10 is scanned by a focussed beam of light 14 which is scanned from edge 11 to edge 12 in the direction of the arrow 16. The beam of light may be provided by a laser beam 17. The incident beam 17 is reflected by the sheet 10 in a generally diffuse nature as is described with respect to FIGS. 1 and 2 of our earlier U.S. Pat. No. 2,117,897.

FIG. 3 shows the surface of the sheet 10 which has an edge or discontinuity 10C caused by a change from a first surface portion 10A to a second surface portion 10B. The discontinuity 10C may be in the form of a crease or other discontinuity. As is described in our earlier U.S. Pat. No. 2,117,897 a beam of radiation in the form of the incident laser beam 17, strikes the surface of the sheet 10 and scatters radiation as is indicated by the short arrows 18.

There is provided means 19 for receiving the scattered radiation from the surface within a wedge of angles indicated by A in FIG. 5 between angular limits B and C with respect to surface of the sheet 10. Whilst the laser beam 17 is to the left of the position illustrated as X in FIG. 5 then scattered radiation indicated by the small arrows 18 can be received by the light receiving means 19. However, whilst the laser beam 17 between the positions X and Y illustrated typically by position Z the light receiving means 19 cannot receive scattered radiation from the surface of the sheet 10 because of the edge 10C between the surfaces 10A and 10B. As a consequence, if the laser is between X and Y no light is received by light receiving means 19 and therefore there is no output from light receiving means 19.

As is explained in our earlier U.S. Pat. No. 2,117,897 if there is provided a second light receiving means 21 which similarly receives radiation only between angular limits D and E then a comparison of the light received by means 19 and 21 will indicate whether the scattered light has been reflected from a normal part of the surface of sheet 10 (in which case comparative values of the light received by means 19 and 21 will be the same, although the absolute values of light received may vary if, for example, the sheet carries printed material) or there is a crease or discontinuity as shown in FIG. 3 in which case the light received by 19 and 21 will be different. In this case the light received by 21 if the laser beam 17 is between X and Y will be greater than that received by means 19.

The use of a comparison between the light received by light receving means 19 and 21 has been utilised in our earlier U.S. Pat. No. 2,117,897 to eliminate the shadows cast by smaller sheets pasted onto a larger sheet in a mock-up of a page of a newspaper.

A further use of comparison of the light received by the light receiving means 19 and 21 is in providing an indication of the height difference between the surface portion 10A and 10B. It will be understood that the linear distance between laser beam position X and Y is dependent upon the height difference (H) between surface parts 10A and 10B. As the height difference increases, so the difference between X and Y increases. Such an arrangement is useful in examining an object where discontinuities such as the step shown in FIG. 3 are likely to be present on the surface of the object being examined and in which a small step, that is a small height H between the surface parts 10A and 10B can be tolerated but a larger step cannot be tolerated. Apparatus of this type, therefore, provides a means for discriminating between acceptable and unacceptable surface irregularities.

The light receiving means 19 will now be described with reference to FIGS. 1 and 2. The light receiving means 19 comprises a first perspex polymethylmethacrylate prism 26 the base 27 of which extends parallel to and above the sheet 10 and extends beyond the edges 11 and 12. A side face 28 of the prism 26 has a matt black surface to absorb light incident on the face 28 from within the prism. The upper face 29 of the prism 26 extends as shown in FIG. 1.

The upper face 29 of the prism 26 spaced from a coplanar lower face 31 of a second perspex polymethylmethacrylate prism 32 by an air gap 25, the second prism 32 having a second upper face 33 which extends from an apex adjacent the apex between the base 27 and upper face 29 of the first prism 26. A third, end face 34 of the second prism is mounted adjacent a photomultiplier 36. A plane mirror 37 is mounted adjacent to and parallel to the upper face 33 there being provided a small air gap 40 between the upper face 33 and the mirror 37. FIG. 1 shows the limiting rays receivable by the light collection means 19 which corresponds to angles B and C in FIG. 5.

Considering the left hand limiting ray, FGHJ, the ray from the diffusing surface is refracted at G on the base surface 27 of the first prism 26, and is totally internally reflected at H on the upper face 29 to be reflected back along line HJ to J on the side face 28 where it is absorbed by the matt black surface.

The other limiting ray FKLMNPQR is refracted at K on the base face 27 of the first prism 26, refracted at L on the upper face 29 and passes across the air gap 25 into the second prism 32 at M, is refracted through the upper face 33 of the second prism 32 at N, is reflected at P by the plane mirror 37, re-enters the second prism at Q, and is refracted at R on the lower face 31 of the second prism. It passes into the air gap 25 at a grazing angle at so will not re-enter the prism 26 and is lost to the system.

Rays between these two limiting rays enter the base face 27, are refracted through the upper face 29 of the first prism 26, cross the air gap 25 and enter the lower face 31 of the second prism 32, and are successively totally internally reflected at the upper face 33 and lower face 31 of the second prism so as to pass up through the second prism 32 to the end face 34 where they enter the photomultiplier 36.

The invention is not restricted to the details of the foregoing example.

If the two prisms are of materials of different refractive indices then the air gap 25 may be eliminated.

As will be understood the two light receiving means 19 and 21 of FIG. 3 may be similar.

In an alternative arrangement, for a different purposes, the photomultiplier 36 may be replaced by a light source which may be a non-coherent light source which will thereby produce light which strikes the surface 11 within the angles defined, in FIG. 1 by the rays FG and FK. The complete length of the surface 11 will be illuminated but with light from this particular angular direction.

I claim:

1. Apparatus for transmitting ony radiation received by the apparatus within predetermined angular limits, the apparatus including:
   a first transparent body including a first surface for receiving radiation;
   said first transparent body including a second surface which, depending on the angle of incidence of the radiation thereon, either reflects by total internal reflection or refracts the radiation incident thereon, the radiation, if totally internally reflected, not being transmitted by the apparatus, and the radiation, if refracted, being passed to a second transparent body;
   said second transparent body being mounted adjacent to said second surface of said first transparent body, radiation passing into said second transparent body from said first transparent body being passed to a first surface of said second transparent body, which, depending on the angle of incidence of the radiation thereon, either reflects by total internal reflection or refracts the radiation incident thereon, radiation refracted from said first surface of said second transparent body not being transmitted by said apparatus, and radiation totally internally reflected from said first surface of said second transparent body being collected by said second transparent body, whereby opposite predetermined angular limits of the receipt of radiation are defined by critical angles at surfaces of the transparent bodies.

2. Apparatus as claimed in claim 1 in which the second transparent body is adapted such that radiation totally internally reflected at said first surface thereof is totally internally reflected a plurality of times at said first surface and at a second surface of said second transparent body.

3. Apparatus as claimed in claim 1 including detector means; and in which said radiation collected by said second transparent body is passed to the detector means.

4. Apparatus as claimed in claim 1 in which the second transparent body is triangular in shape; and the radiation when internally reflected, is directed towards a smaller side of said second transparent body; and including detector means situated at said smaller side of said second transparent body.

5. Apparatus as claimed in claim 1 characterised in that said two transparent bodies comprise prisms (26,32).

6. Apparatus as claimed in claim 1 characterized in that radiation refracted into said second transparent body (32) is refracted out of said body (32) through a second surface (33), is reflected by a mirror (37), and re-enters the transparent block (32), before passing to said first surface (31).

7. Apparatus as claimed in claim 6 characterized in that an air gap (25) is provided between said two transparent bodies (26,32), said surfaces (29,31) are planar and are arranged parallel to and adjacent to one another with said air gap (25) therebetween, whereby radiation refracted through said first surface (31) is reflected out of said apparatus through said air gap (25) by means of external reflection at the surfaces (29,31).

8. Apparatus as claimed in claim 1 characterised by radiation detector means (36) arranged to collect said radiation between said predetermined angular limits.

9. Apparatus for only transmitting radiation received within predetermined angular limits, the apparatus including means to which the received radiation is passed, the opposite predetermined angular limits within which the received radiation is transmitted being defined by total internal reflection within the apparatus, said apparatus further including:
 a first transparent body arranged to receive radiation, and including a surface for reflecting by total internal reflection or refracting radiation incident thereon, refracted radiation being collected by the apparatus and reflected radiation being absorbed, whereby the critical angle of total internal reflection of said surface defines one of said predetermined angular limits,
 a second transparent body mounted adjacent to said surface, whereby radiation refracted by said surface passes into said second transparent body, the radiation passing into said second transparent body being passed to a first surface of said second transparent body, said radiation incident on said first surface being refracted therethrough or internally reflected therefrom, said refracted light being totally lost to the system and said totally internally reflected radiation being collected by the apparatus, in which the radiation refracted into said second transparent body is refracted out of said body through a second surface, is reflected by a mirror, and re-enters the second transparent body, before passing to said first surface.

10. Apparatus for only transmitting radiation received within predetermined angular limits, the apparatus comprising:
 input means for receiving radiation,
 at least two transparent bodies, and
 an output incorporating radiation detector means,
 opposite angular limits both being defined by the critical angle of total internal reflection at surfaces of said transparent bodies,
 said second transparent body being shaped so as to direct radiation totally internally reflected by said second transparent body to the radiation detector means.

11. Apparatus for only transmitting radiation received within predetermined angular limits, comprising first and second transparent body means, the angular limits being defined by the critical angle of reflection at surfaces of said first and second transparent body means, whereby radiation received at an angle less than a lower limit is totally internally reflected by a surface of said first transparent body means and then absorbed, radiation received between said limits is passed to detector means by total internal reflection from a least one surface of said second transparent body means and radiation received at an angle greater than a second upper limit is refracted by said second transparent body means and is totally lost to the system.

* * * * *

UNITED STATES PATENT AND TRADEMARK OFFICE
CERTIFICATE OF CORRECTION

PATENT NO. : 4,851,696

DATED : July 25, 1989

INVENTOR(S) : Robert N. West

It is certified that error appears in the above-identified patent and that said Letters Patent is hereby corrected as shown below:

In the Specification:

Column 1, line 27, after "separately is" insert -- that they can be moved around to change the layout --.
Column 1, line 33, change "the" to -- that --. (2nd occurr.)
Column 1, line 56, change "dirrection" to -- direction --.

Column 3, line 45, change "corresponds" to -- correspond --.

In the Claims

Column 4, line 18, change "ony" to -- only --.

Column 6, line 32, change "a" to -- at --.

Signed and Sealed this

Twenty-first Day of August, 1990

*Attest:*

HARRY F. MANBECK, JR.

*Attesting Officer*     *Commissioner of Patents and Trademarks*